United States Patent [19]

Vaughan

[11] 3,976,704

[45] Aug. 24, 1976

[54] NITRATION PROCESS

[75] Inventor: Ronald J. Vaughan, Claremont, Calif.

[73] Assignee: Varen Technology, Marshallton, Del.

[22] Filed: Jan. 6, 1975

[21] Appl. No.: 538,723

[52] U.S. Cl. .................. 260/645; 204/296; 260/562 R; 260/578; 260/612 D; 260/622 R; 260/646; 260/647; 260/688
[51] Int. Cl.² ........................ C07C 79/10
[58] Field of Search ............. 204/296; 23/266; 260/645, 612 D, 562 R, 578, 622, 647, 688

[56] References Cited
UNITED STATES PATENTS

| | | | |
|---|---|---|---|
| 3,714,272 | 1/1973 | Coon et al. | 260/645 |
| 3,887,499 | 6/1975 | Hodgdon | 204/296 |

OTHER PUBLICATIONS

Urbanski, *Chemistry and Technology of Explosives*, vol. 1, The Macmillan Co., New York, 1964, pp. 86 and 133.

*Primary Examiner*—Leland A. Sebastian
*Attorney, Agent, or Firm*—Robert J. Baran

[57] ABSTRACT

This invention relates to a process for the nitration of organic compounds, especially aromatic compounds, which comprises contacting said compound with a nitrating agent at conditions whereby a nitrated product is formed. The nitration agent and the compound are substantially separated by means of a polymeric membrane, said polymeric membrane preferably comprising sulfonic acid groups, pendant to the polymeric backbone. In a most preferred embodiment, the membrane is a perfluorosulfonic acid polymer. The use of this most preferred polymeric material as a membrane in the instant process allows the nitration of aromatic organic compounds to take place without the incorporation of strong sulfuric acid in the nitrating agent.

10 Claims, No Drawings

NITRATION PROCESS

FIELD OF THE INVENTION

This invention relates to a process for the nitration of organic compounds, especially aromatic compounds, which comprises contacting said compound with a nitrating agent at conditions whereby a nitrated product is formed. The nitration agent and the compound are substantially separated by means of a polymeric membrane. This membrane is a polymeric material, preferably comprising sulfonic acid groups pendant to the polymeric backbone. In a most preferred embodiment, the membrane is a perfluorosulfonic acid polymer. The use of this most preferred polymeric material as a membrane in the instant process allows the nitration of aromatic organic compounds to take place without the addition of strong sulfuric acid to the nitrating medium. The instant process also allows nitration to occur while maintaining separation of the aromatic compound from the nitrating medium, thus product recovery is facilitated.

SUMMARY OF THE PRIOR ART

It is known in the art that aromatic compounds may be nitrated by reacting said compound in a mixture of nitric and sulfuric acid. A strongly acidic medium is necessary in this prior art process to promote the rate of nitronium ion formation since nitric acid increasingly becomes an oxidant as the acidity decreases. It is also desirable, and known in the art, to maintain the water content of the nitrating agent at a low level to obtain a maximum rate of reaction.

In a most preferred embodiment of the instant invention, a perfluorosulfonic acid polymer is used as a membrane to separate nitric acid from the aromatic compound which is to undergo nitration. This polymeric material with its pendant sulfonic acid groups allows nitration to proceed without the addition of sulfuric acid to the nitric acid.

Furthermore, although the acidity of the nitric acid, typically, changes from 15M to 11M during the course of the nitration reaction due to the formation of water of reaction, the presence of the pendant sulfonic acid groups at the membrane interface allows nitration to proceed under conditions at which $HNO_3$ usually is more of an oxidant.

Furthermore, the membrane in the process of the instant invention can be of a tubular shape and, as further described below, arranged in a heat exchange configuration. That is, a second membrane, in a tubular shape can be disposed in concentric relationship around the tubular, perfluorosulfonic acid polymer membrane. In this embodiment, the nitrating medium can be flowed in a concurrent or countercurrent manner through the interior of tubular perfluorosulfonic acid polymer membrane or in the annular space between said tubular membrane and said second membrane. This heat exchange configuration provides facile control of a very exothermic reaction.

An example of the prior art processes for the nitration of aromatics is found in U.S. Pat. No. 2,849,497. It should be noted that this process teaches the nitration of benzene in a two-phase mixture wherein an aqueous solution of sulfuric acid and a nitric acid is contacted with benzene by means of emulsifying the mixture. Emulsification is necessary to increase contact of the benzene and the aqueous nitration solution since benzene is substantially insoluble in aqueous nitric acid-sulfuric acid solutions. It may be seen from the outline of the process described in FIG. 1 that a settling step, i.e., an emulsion breaking step must be incorporated into the process flow scheme so as to separately work the organic and aqueous phases after nitration. In the instant process wherein the aqueous and organic phases are mantained substantially separate throughout the nitration, this settling step, of course, is eliminated. In the instant process wherein the organic compound and the nitration agent must contact across a membrane, adequate surface area for said contacting may be flexibly obtained by design of the membrane and choice of the material in forming said membrane.

SUMMARY OF THE INVENTION

The instant invention relates to a process for the nitration of organic compounds, especially organic, aromatic compounds. In this process, the compound which is to undergo the nitration reaction is contacted with nitration agent across a membrane which substantially maintains the organic compound separate from the nitration agent. The nitration agent may be nitrogen oxide, i.e., $N_2O_4$, but preferably nitric acid, generally present as an aqueous nitric acid solution, is used as a nitrating agent.

The process of the instant invention may be conveniently carried out in a diffusion cell which comprises a chamber which is divided into separate compartments by means of a membrane. Each compartment will have means for bringing a fluid into said compartment and means for removing it therefrom. The process may be carried out continuously or batchwise, but preferably in a continuous manner. The membrane is a polymeric material, preferably having sulfonic acid groups, pendant from the polymer backbone. In the most preferred embodiment, the membrane is a perfluorosulfonic acid polymer.

The membrane may be utilized in various shapes and thicknesses, for example, hollow fibers, tubes, planar, etc. shaped membranes may be placed in a diffusion cell so as to form the separate compartments. The membrane may vary in thickness from 0.0001 to 0.040, preferably from 0.001 to 0.010 inch. The thickness of the membrane will be chosen with a view toward ease of fabrication and maintenance during the process of the instant invention in an integral form.

The organic compound which is present as a liquid, i.e., either in solution or neat is contacted with the nitration agent in a countercurrent or concurrent manner. The nitration agent may be in a gaseous or liquid form, but is preferably a liquid.

The contacting of the organic compound and the nitration agent may be designed by those skilled in the art to obtain various degrees of conversion per pass. In general, longer times of contact and decreased membrane thicknesses promote increased conversion. It is also noted, as hereinbelow described, that the temperature at which the contact takes place substantially affects the degree of conversion. That is, as the temperature increases so does the conversion. The time of contact of the nitration medium with the organic compound may be varied by either decreasing the flow rate or increasing the size or area of contact in the diffusion cell. It is also noted and hereinafter described below that within the limits of concentration of nitric acid (the preferred nitration agent) preferred for use in this process increase of flow has substantially no effect. Finally, the concentration of the nitration medium and when in solution the concentration of the organic compound may substantially affect the conversion. Notwithstanding the above, it has unexpectedly been found that at high concentrations of nitric acid in the aqueous nitration solution increasing the temperature does not increase the conversion of the aromatic compound. This unexpected result is more fully described below.

The compounds which are useful for nitration in the process of the instant invention are those well known in the art. For example, aromatic compounds are generally preferred for use in the instant process since they undergo convenient nitration reactions to form nitrated products having a great degree of utility. The aromatic compounds may be hydrocarbons or the substituted derivatives thereof. In general, the aromatic compounds will have from 6 to 20 carbon atoms and may be substituted by groups, the heteroatoms of which may be selected from the group consisting of nitrogen, oxygen, silicon, phosphorus, sulfur and the halogens. For example, the instant process may be utilized to nitrate aromatic compounds which contain amino, nitroso, chlorine, fluorine, bromine, silano, ether, hydroxy, carboxyl, etc. type groups. The specific examples of aromatic materials which may be nitrated by the instant process include benzene, toluene, ortho-, meta- and paraxylene, anisole, phenol, naphthalene, acetanilide, and other nitratable aniline derivatives, etc. Further examples of materials which undergo nitration reactions may be found in *Nitration of Hydrocarbons and Other Organic Compounds*, A. V. Topchiev, Pergamon Press, 1959. The material which is to undergo nitration, if a liquid, is preferably used neat so as to minimize any undesirable side reactions with a solvent. The material, if a solid at room temperature, may be heated to a temperature at which it may be nitrated as a melt. For example, the nitration process may take place at temperatures of up to 200°C. Thus, materials which are molten and substantially fluid at temperatures up to this limit may be utilized.

Materials which cannot be fluidized by temperature can be dissolved in a suitable solvent and used in this manner. The use of a solvent is generally more preferable than heating to high temperatures to fluidize a solid reactant. It is, of course, obvious to the skilled artisan that the solvent will have to be selected so as to minimize any interference with the nitration agent and/or the membrane material at the temperatures of reaction. The solvent also should be immiscible with the nitration agent so as to maintain the phase separation which provides one of the advantages of the instant process. Examples of suitable solvents include nitrobenzene, dichlorobenzene, cyclohexane, $CCl_4$, etc.

The nitration agent described above may be selected from those that are known in the art, for example, nitric acid, dinitrogen tetraoxide, nitric acid-acetic anhydride mixtures, and salts of the nitronium ion, e.g., nitronium tetrafluoroborate. Preferably, the nitration agent comprises an aqueous, nitric acid solution. The aqueous, nitric solution may contain from 5 to 100 weight percent nitric acid. Preferably, the nitric acid content of said solution will be from 50 to 95 weight percent $HNO_3$. Sulfuric acid may be incorporated in the nitrating medium in any percent desired; however, it should be noted that, unlike the prior art processes wherein mixtures of 2 parts 96 weight percent sulfuric acid with one part 70 weight percent nitric acid yields optimum results, it is found in the instant invention that this particular ratio yields much poorer conversions than the substantially decreased ratio of 1 to 1. If desirable sulfuric acid may be incorporated in the nitration agent at an amount varying from 0 to 80 weight percent.

It may also be desirable to incorporate other materials in the nitration agent since the presence of water is deleterious to the nitration reaction. For example, dehydrating agents, such as acetic anhydride, may be incorporated.

It will be apparent to the skilled artisan that the advantages of the process of the instant invention inhere from the use of a membrane to substantially isolate the nitration agent and the organic compound which is to undergo the nitration reaction while allowing the contacting of these two reactants across the membrane. Thus, it is clear that the membrane must be designed so as to allow the nitration agent and the organic compound to come into contact at the interface formed by the membrane. The membrane must also be substantially chemically inert to the action of both the organic compound and the nitration agent so as to maintain its integrity and thus its function as a separations device. Materials which are chemically inert to the organic compound and the nitration agent at the temperatures at which the reaction will take place must be used in the membrane. These materials must also be capable of being fabricated into membranes having minimum thicknesses so as to obtain the conversion desired without long reaction times. Because of their inertness, fluorinated polymers have been found to be very suitable for use in the process of the instant invention. It has been mentioned above that the process of the instant invention may be carried out in the absence of sulfuric acid if sulfonic acid groups are incorporated into the membrane material. Thus, in the most preferred embodiment of the instant invention, the membrane comprises a perfluorosulfonic acid polymer. These materials are described in U.S. Pat. Nos. 3,041,317; 3,282,875; and 3,624,053, herein incorporated by reference. This material is preferred for use in the present process because of its inertness to the reactants at the conditions at which the reaction is taking place, its ease of fabrication into suitable membranes and its ability to take part in the nitration process so as to eliminate the need for sulfuric acid. It should be noted that if the sulfuric acid is eliminated from the nitration process, materials used to construct the reactors, that is the diffusion cell described above may be selected on a more economical basis, for example, elimination of sulfuric acid cuts down corrosion and thus stainless steel rather than the usual materials, i.e. lead lined, glass lined, ceramic or special cast iron reactors used in the prior art processes, may be utilized.

The perfluorosulfonic membrane may be utilized in the form of sheets, tubes and hollow fibers. The material may be laminated to scrim to allow for more dimensional stability. The material may be incorporated into the diffusion cell by supported or unsupported means; for example, when hollow fibers are utilized other than at the point where a hollow fiber enters and exits from the diffusion cell there is no need, in general, for support. When the membrane material is present as a sheet, it may be supported on a stainless steel screen, on a porous metal surface, or on an inert fabric material which allows free passage of both reactants and products.

It has been found that when the preferred perfluorinated sulfonic acid polymer is used as the membrane that the equivalent weights of the polymer have an important effect on the conversion, that is it has been found that the lower equivalent weights, every other variable being equal, yield increased conversion. Equivalent weight is defined as the weight of the membrane polymer per sulfonic acid group in grams. It has been found that weights as low as 1060 give optimum results, while the higher weights, that is 1340 and above, show decreased conversions. The practical minimal equivalent weight which may be used in polymers is about 900. At weights below this, difficulties arise in fabrication and mechanical properties of fluorinated sulfonic acid polymer films, hollow fibers, tubes, etc.

The process of the instant invention is carried out at reaction conditions which are similar to the prior art processes, that is the temperature at which the nitration process may be run varies from the freezing point of either the organic compound or the nitration medium or the mixture of organic compound and solvent, if used, and the boiling point of any of the components at the pressures employed. Thus, the process may be carried out over broad temperature and pressure ranges. It has been found that increasing the temperature increases the conversion rate. However, the upper limit depends on the interference of competitive reaction and inertness of the membrane material to temperature. It has been found that when using the process of the instant invention, unlike the prior art, competing reactions are minimized. Thus, it is possible to go to higher temperatures and achieve the greater rates of converison with the instant process than with the prior art process. For example, it has been found in the case of benzene that very little oxidation and dinitration takes place even at temperatures up to 100°C. if the other variables are carefully controlled. In general, the process of the instant invention is carried out at pressures of from 0 to 200 psi and temperatures of from 0° to 200°C. Preferably, the ambient or slightly elevated pressures are utilized while the temperature is maintained at from about 40°C. to 150°C. More preferably, the process is carried out at from 70°C. to 100°C.

The nitrated compounds prepared by the process of the instant invention have well known uses. For example, nitrobenzene may be used to prepare aniline, a useful chemical intermediate in the preparation of dyes, etc. Nitrotoluene is useful as a chemical intermediate or in the preparation of explosives, or polymeric materials, such as urethane rubbers.

The following are preferred embodiments of the instant invention. However, there is no intent to be limited by other than the scope of the claims.

The apparatus used in the nitration experiments described below consisted of a tubular flow reactor in an annular design. This reactor comprises an inner tube of a perfluorosulfonic acid polymer (0.024 ID × 0.036 inch OD × 26 or 38 feet long) and an outer tube of Teflon (1-1/6 ID × ⅛ inch OD). The reactants were introduced and withdrawn separately from the inner tube or from the annular shell between the inner tube and the inner wall of the outer tube. This composite tube was coiled around a cylinder of stainless steel screening and immersed in a stirred resin kettle filled with distilled water. Means for flowing fluids through the tube was provided and a flow meter to measure said flow. The flow rate was adjusted with a metering valve on the exit of the reactor described above. The pressure of the reactants was either atmospheric pressure in which case flow was provided by a calibrated syringe pump or the pressure of a pressurized tank containing the reactant. The products of the reaction were collected in test tubes at room temperature and samples withdrawn and analyzed immediately. Positive analysis was performed by gas chromatography. The hydrocarbon samples were diluted with an aliquot of benzene containing a known concentration of 4-chlorobenzonitrile as an internal standard for this analysis.

EXAMPLE 1 — Benzene with 70% Nitric Acid

The annular tube reactor was equilibrated with benzene in the "outer tube" and 70% nitric acid in the "inner tube" at flow rates of 0.25 ml/min and 0.13 ml/min, respectively, a temperature of 85°, and a pressure of 12 psi. Effluent from the exits of the reactor was collected in tared receivers. The material balance was as follows:
Introduced: Benzene 77.1 g, Nitric Acid 70.7 g (Total 147.8 g)
Received: Organic Phase 90.15 g, Aqueous Phase 54.9 g (Total 145.1 g)

The organic phase was washed with 1M sodium hydroxide (only traces of nitrophenoxide ion color observed), then with brine. Distillation first through a Vigreaux column at atmospheric pressure, then through a simple Claisen head under vacuum yielded nitrobenzene as the sole high-boiling component (69°C. (4.4 mm), 22.4 g. 18.5% conversion). The infrared spectrum and retention time on the gas chromatography columns were identical to an authentic sample.

EXAMPLE 2 — Benzene and Fuming (90%) Nitric Acid

The empty tubular reactor was filled at 40°C. with fuming nitric acid (outer tube) and benzene (inner tube). The reactor was heated quickly to 85° and flow was started through both tubes (using 10–12 psi nitrogen pressure) at flow rates of 0.5 ml/min and 0.3 ml/min for the benzene and nitric acid respectively. The effluent organic and aqueous phases were collected in separate tared receivers. Material balance was as follows:
Introduced: Benzene 72.7 g, Nitric Acid 84 ml, Specific Gravity 1.5 = 126 g (Total 198 g)
Effluent: Organic Phase 147.4 g, Aqueous Phase 51.1 g (Total 198 g)

Benzene was added to the organic phase and to the aqueous phase. The combined benzene phases were extracted with brine, then distilled through a Vigreaux column at atmospheric pressure. The residue was distilled at reduced pressure to yield nitrobenzene (85.1 g, 82% conversion) and a small solid residue (1 g) of nitrophenol.

EXAMPLE 3 — Process Variables in the Nitration of Benzene

Runs were made varying temperature, flow rate, and concentration of nitric acid. Additionally, the effect of the addition of $H_2SO_4$ to the nitric acid was studied. The results are reported in Table I below.

TABLE I

| | Temperature (°C.) | Concentration HNO₃ (% w/w) | Benzene Flow (ml/min) | HNO₃ Flow (ml/min) | Benzene Location (Inner/Outer) | Nitrobenzene (% w/v) |
|---|---|---|---|---|---|---|
| a) | 60° | 70% | 0.8 | 0.26 | Inner | 3.3 |
| | 70° | 70% | 0.8 | 0.26 | Inner | 4.5 |
| | 75° | 70% | 0.8 | 0.26 | Inner | 6.3 |
| | 80° | 70% | 0.8 | 0.26 | Inner | 8.1 |
| b) | 70° | 70% | 0.5 | 0.26 | Outer | 10.1 |
| | 80° | 70% | 0.5 | 0.26 | Outer | 11.7 |
| | 85° | 70% | 0.5 | 0.26 | Outer | 14.5 |
| | 90° | 70% | 0.5 | 0.26 | Outer | 17.7 |
| | 97° | 70% | 0.5 | 0.26 | Outer | 23.0 |
| c) | 70° | 70% | 2.0 | 0.26 | Inner | 1.5 |
| | 70° | 70% | 0.5 | 0.26 | Inner | 7.9 |
| | 70° | 70% | 0.2 | 0.26 | Inner | 21.4 |
| d) | 70° | 70% | 0.5 | 0.13 | Inner | 8.2 |
| | 70° | 70% | 0.5 | 0.26 | Inner | 7.9 |
| | 70° | 70% | 0.5 | 0.51 | Inner | 9.9 |
| e) | 70° | 70% | 0.5 | 0.26 | Inner | 7.9 |
| | 70° | 80% | 0.5 | 0.26 | Inner | 22.7 |
| | 70° | 90% | 0.5 | 0.26 | Inner | 35.9 |
| f) | 70° | 70% | 0.5 | 0.26 | Inner | 9.4 |
| | 70° | 1:1 (Wt/Wt) H₂SO₄:70% HNO₃ | 0.5 | 0.26 | Inner | 13.9 |
| | 70° | 2:1 (Wt/Wt) H₂SO₄:70% HNO₃ | 0.5 | 0.26 | Inner | 6.1 |
| g) | 70° | 90% | 0.5 | 0.2 | Outer | 56% |
| | 80° | 90% | 0.5 | 0.2 | Outer | 58% |
| | 85° | 90% | 0.5 | 0.2 | Outer | 55% |
| | 90° | 90% | 0.5 | 0.2 | Outer | 61% |
| | 98° | 90% | 0.5 | 0.2 | Outer | 51% |

Concurrent flow of 70% nitric acid and benzene through the tubular reactor on opposite side of the membrane led to the conversion of some of the benzene to nitrobenzene; at constant flow rates, increased temperature led to increased conversion. (See Table I, a, b.) Even at the highest temperature employed (97°C.), no dinitrobenzene could be detected. Decreasing the flow rate of the benzene phase increased conversion to nitrobenzene (Ic), whereas increasing the flow rate of the nitric acid phase has relatively little effect on conversion (Id). This suggests that the principal factor limiting conversion is not depletion of the nitric phase, but a rate-limiting production of the nitrating species.

Increased nitric acid concentration led to increased conversion to nitrobenzene (Ic).

The combination of increased acidity and decreased water concentration created by increasing sulfuric acid concentration usually leads to increased rates of nitration. However, while addition of sulfuric acid at a 1:1 (wt/wt) ratio slightly increased conversion, a mixture of 2:1 (wt/wt) sulfuric acid-70% nitric acid (the usual mixed-acid nitrating mixture decreased conversion to nitrobenzene (If).

Reactions with 90% nitric acid led to high single-pass conversions of benzene to nitrobenzene (Ig). Increasing temperature in this case did not lead to increased conversion in the temperature range investigated (70°–98°C.), suggesting that conversion is limited by depletion of the nitric acid phase.

"Static" nitrations were conducted in two-compartment stainless steel cells comprising two mating circular halves of identical cavity dimensions 0.6 × 37 cm separated by an unreinforced perfluorosulfonic acid polymer membrane clamped between the two halves. After assembly, nitric acid was placed in one-half of the cell and the cell was placed on a shaking platform immersed in a water bath and allowed to equilibrate at the desired reaction temperature. Reaction was initiated by addition of the aromatic hydrocarbon to the other side of the cell. (Due to the long reaction times involved, no attempt was made to preequilibrate the hydrocarbon at the reaction temperature).

The samples were collected and analyzed as above with the exception that cyclohexanone was used as the internal standard for nitrotoluene.

EXAMPLE 4 — Nitration of Benzene

A. Effect of Temperature

The static nitration of benzene at 60° and 70°C. is presented in Tables III and IV respectively using 70% nitric acid as the nitrating agent. The reaction is appreciably slower at 60°C. than at 70°C. (9% w/v nitrobenzene at 400 minutes vs 18%).

B. Effect of Nitric Acid Concentration

Nitration at higher acid concentration is appreciably faster, as shown in Tables IV and V (70% and 90% HNO₃ respectively). The difference is most apparent in the initial portion of the reaction (4% vs 36% w/v at 100 minutes) before depletion of the nitric acid decreases the difference in rate. In this case, the final measured product concentrations at longer times were not greatly different (41% vs 50% w/v).

C. Effect of Membrane Equivalent Weight

A series of perfluorosulfonic acid polymer membranes of the same thickness 0.004 inches (4 mil) and increasing equivalent weight (weight of membrane polymer per sulfonic acid group in grams) was obtained from DuPont, Wilmington, Delaware. Nitration of benzene at 70° using 70% nitric acid is shown for the series in Tables VI–VIII. Nitration was slower at higher equivalent weight of the membrane (at 400 minutes, 1100 E.W. = 25% w/v; 1200 E.W. = 23% w/v; 1340 E.W. = 15% w/v).

EXAMPLE 5 — Nitration of Toluene and Anisole

Nitration of toluene and anisole at 60° with 70% nitric acid is shown in Tables IX and X. Comparison with benzene at 60°C. (Table III) shows the considerable increase in nitration rate with the more reactive aromatics.

The other variables previously explored in the flow reactor system appear to have the same effect in static nitration. The rate increases with temperature, effectively doubling the initial rate in going from 60° to 70° in the case of benzene; increased rate is also observed for increased nitric acid concentration.

Nitration of toluene and anisole proceeded at considerably faster rates than benzene in the static cells; however, the rate increases are far less than would be anticipated based on the known relative reactivities of these aromatics toward nitration (at 400 minutes, at 60°, nitrobenzene = 9% w/v; nitrotoluene = 14%; nitroanisole = 26% w/v). At high flow rates, product concentration is roughly inversely proportional to flow rate. At low flow rates, a "plateau" is reached in product concentration in which rate is effectively limited by low nitric acid concentration. The rate decreases markedly at about 12M nitric acid, and essentially ceases at 8 molar acid.

EXAMPLE 6 — Nitration of Toluene in Tubular Flow Reactor

Continuous nitration of toluene was conducted in a tubular flow reactor similar to the one described above except that the dimensions of the inner tube (polyfluorosulfonic acid) were 0.025 ID × 0.035 inch OD, and the outer were 0.062 ID × 0.125 inch OD. The length of the tubes were 38 feet.

Nitration of toluene was conducted in the tubular flow reactor varying flow rate, ratio of toluene to nitric acid flow rate, temperature and nitric acid concentration. The results of these studies are presented in Table II.

Some oxidation to benzaldehyde (~1%) was observed; no dinitration products and very little, if any, other oxidation products were detected. Thus, one of the most desirable characteristics of the instant process seems to be the virtual absence of reactions other than mononitration usually observed; presumably dinitration could be expected in this system with greater than 90% nitric acid and higher temperatures, however.

EXAMPLE 7 — Preparation of Nitrotoluene in a Tubular Flow Reactor

The annular tube reactor was equilibrated with toluene in the inner tube and 70% nitric acid in the annular channel at flow rates of 0.33 ml/min and 0.13 ml/min respectively, a temperature of 80°C. and a pressure of 10 psi. Effluents were collected from both sides. Material balance was:

| Into reactor: | | Out of reactor: | |
|---|---|---|---|
| Toluene | 50.4 g. | Toluene Phase | 58.7 g. |
| 70% Nitric Acid | 29.7 g. | Nitric Acid | 24.1 g. |
| | 80.1 g. | | 82.8 g. |

(The slight discrepancy is due to difficulties in returning the reactor to a "standard state" under flow conditions).

The organic phase was washed with water, saturated sodium bicarbonate solution, then sodium carbonate solution to remove acid (see below), then distilled into a cooled receiver at low pressure (0.25 mm) leaving a small amount of liquid residue (65 mg, not analyzed; presumably containing all the dinitration products). Redistillation through a vacuum-jacketed Vigreaux column yielded the nitrotoluene fraction boiling at 97°-109°C. (4 mm) (11.76 g. 16% yield based on toluene introduced) and a small pot residue.

Acidification of the aqueous layers from extraction of the organic phase yielded a precipitate which was collected in a tared filter crucible and dried in vacuo (37 mg, not analyzed, probably mixed nitrophenols and benzoic acid).

Titration of the acid phase from the reactor indicated a value of 11.1M for the final acid concentration (15.5M starting) from the nitration zone.

TABLE II

FLOW NITRATION OF TOLUENE

A. Variation of Flow Rate (T = 70°C., 70% HNO₃)

| Flow (ml/min, both sides) | Sum of Nitrotoluenes (% w/v) | Benzaldehyde (% w/v) | Conc. Final Acid (Molar) |
|---|---|---|---|
| 0.26 | 30.7 | 0.75 | 12.3 |
| 0.51 | 26.6 | 0.43 | 12.7 |
| 0.71 | 20.0 | 0.30 | 12.5 |
| 1.0 | 16.7 | 0.28 | 12.8 |

B. Variation of Temperature (Flow Rate 0.51 ml/min both sides, 70% HNO₃)

| Temperature (°C.) | Sum of Nitrotoluenes (% w/v) | Benzaldehyde (% w/v) | Final Acid (Molar) |
|---|---|---|---|
| 50° | 12.2 | 0.19 | 13.7 |
| 60 | 17.6 | 0.19 | 12.9 |
| 70 | 23.7 | 0.31 | 12.3 |
| 80 | 28.1 | 0.57 | 11.6 |

C. Variation of Ratio of Flow Rates (T = 70°C., 70% HNO₃)
Toluene Flow = 0.51 ml/min

| HNO₃ Flow (ml/min) | Sum of Nitrotoluenes (% w/v) | Benzaldehyde (% w/v) | Final Acid (Molar) |
|---|---|---|---|
| 0.26 | 17.1 | 0.15 | 8.33 |
| 0.51 | 25.2 | 0.31 | 12.4 |
| 1.0 | 25.5 | 0.62 | 13.0 |

HNO₃ Flow = 0.51 ml/min

| Toluene Flow (ml/min) | Sum of Nitrotoluenes (% w/v) | Benzaldehyde (% w/v) | Final Acid (Molar) |
|---|---|---|---|
| 0.26 | 44.5 | 0.68 | 12.4 |
| 0.51 | 25.2 | 0.31 | 12.4 |

TABLE II-continued

| 1.0 | 11.1 | 0.20 | 12.3 |

D. Variation of Acid Concentration (70°C., Flow Rate 0.51 ml/min, both sides)

| (HNO₃) (% w/w) | Sum of Nitrotoluenes (% w/v) | Benzaldehyde (% x/v) | Final Acid (Molar) |
|---|---|---|---|
| 41 | 0.30 | 0 | 7.56 |
| 70 | 25.2 | 0.31 | 12.4 |
| 80 | 52.4 | 0.42 | 12.6 |
| 90 | ~100% w/w | 0 | 11.8 |
| 55% containing | 0.32 | 0 | 10.4 |
| (0.2% CuO | | | |
| (0.05% V₂O₅ | | | |
| (0.05% Cu | | | |

TABLE III

STATIC NITRATION OF BENZENE

Conditions:
- Temperature = 60°C.
- Nitric Acid Concentration = 70%
- Initial Acid Concentration = 15.5 M
- Final Acid Concentration = 11.8 M Membrane: Perfluorosulfonic Acid Polymer
- Thickness 5 mil.
- Equivalent Weight 1200

| Nitrobenzene on Benzene Side (% wt./vol.) | Reaction Time (minutes) |
|---|---|
| 0.5 | 40 |
| 0.5 | 60 |
| 0.6 | 70 |
| 2.0 | 110 |
| 3.2 | 180 |
| 5.3 | 240 |
| 6.6 | 300 |
| 7.8 | 340 |
| 23.4 | 1320 |
| 25.3 | 1440 |
| 24.9 | 1560 |
| 27.2 | 1680 |

TABLE IV

STATIC NITRATION OF BENZENE

Conditions:
- Temperature = 70°C.
- Nitric Acid Concentration = 70%
- Initial Acid Concentration = 15.5 M
- Final Acid Concentration = 13.01 M Membrane: Perfluorosulfonic Acid Polymer
- Thickness 5 mil.
- Equivalent Weight 1200

| Nitrobenzene on Benzene Side (% wt./vol.) | Reaction Time (minutes) |
|---|---|
| 0.8 | 10 |
| 1.0 | 30 |
| 1.2 | 40 |
| 1.8 | 60 |
| 3.6 | 70 |
| 4.7 | 110 |
| 5.2 | 120 |
| 5.7 | 140 |
| 8.0 | 160 |
| 7.5 | 180 |
| 8.6 | 200 |
| 9.4 | 220 |
| 12.4 | 280 |
| 15.5 | 340 |

TABLE V

STATIC NITRATION OF BENZENE

Conditions:
- Temperature = 70°C.
- Nitric Acid Concentration = 90%
- Initial Acid Concentration = 20.7 M
- No Final Acid Concentration Was Made Membrane: Perfluorosulfonic Acid Polymer
- Thickness 5 mil.
- Equivalent Weight 1200

| Nitrobenzene on Benzene Side (% wt./vol.) | Reaction Time (minutes) |
|---|---|
| 0.6 | 0 |
| 1.5 | 5 |
| 3.4 | 10 |
| 5.4 | 15 |
| 7.4 | 20 |
| 11.0 | 30 |
| 10.5 | 40 |
| 17.0 | 50 |
| 23.2 | 60 |
| 24.5 | 70 |
| 36.0 | 100 |
| 35.3 | 120 |

TABLE VI

STATIC NITRATION OF BENZENE

Conditions:
- Temperature = 70°C.
- Nitric Acid Concentration = 70%
- Initial Acid Concentration = 15.5 M
- Final Acid Concentration = 10.6 M Membrane: Perfluorosulfonic Acid Polymer
- Thickness 5 mil.
- Equivalent Weight 1100

| Nitrobenzene on Benzene Side (% wt./vol.) | Reaction Time (minutes) |
|---|---|
| 0.8 | 15 |
| 2.3 | 30 |
| 3.5 | 50 |
| 4.6 | 60 |
| 6.5 | 80 |
| 7.5 | 100 |
| 8.3 | 120 |
| 9.9 | 140 |
| 11.5 | 160 |
| 13.3 | 200 |
| 17.3 | 250 |
| 21.5 | 300 |
| 22.5 | 360 |
| 26.5 | 430 |

TABLE VII

STATIC NITRATION OF BENZENE

Conditions:
- Temperature = 70°C.
- Nitric Acid Concentration = 70%
- Initial Acid Concentration = 15.5 M
- Final Acid Concentration = 13.01 M Membrane: Perfluorosulfonic Acid Polymer
- Thickness 5 mil.
- Equivalent Weight 1200

Nitrobenzene on Benzene Side          Reaction Time

TABLE VII-continued
STATIC NITRATION OF BENZENE

| (% wt./vol.) | (minutes) |
|---|---|
| 0.8 | 10 |
| 1.0 | 30 |
| 1.2 | 40 |
| 1.8 | 60 |
| 3.6 | 70 |
| 4.7 | 110 |
| 5.2 | 120 |
| 5.7 | 140 |
| 8.0 | 160 |
| 7.5 | 180 |
| 8.6 | 200 |
| 9.4 | 220 |
| 12.4 | 280 |
| 15.5 | 340 |
| 25.5 | 430 |

TABLE VIII
STATIC NITRATION OF BENZENE

| Conditions: | Temperature | = 70°C. |
| | Nitric Acid Concentration | = 70% |
| | Initial Acid Concentration | = 15.5 M |
| | Final Acid Concentration | = 11.2 M |
| Membrane: | Perfluorosulfonic Acid Polymer | |
| | Thickness | 5 mil. |
| | Equivalent Weight | 1340 |

| Nitrobenzene on Benzene Side (% wt./vol.) | Reaction Time (minutes) |
|---|---|
| 0.2 | 10 |
| 0.6 | 30 |
| 0.9 | 50 |
| 1.2 | 60 |
| 1.6 | 80 |
| 2.6 | 100 |
| 3.6 | 120 |
| 4.5 | 140 |
| 6.3 | 180 |
| 7.4 | 200 |
| 9.3 | 240 |
| 11.5 | 300 |
| 14.5 | 360 |
| 14.2 | 420 |

TABLE IX
STATIC NITRATION OF TOLUENE

| Conditions: | Temperature | = 70°C. |
| | Nitric Acid Concentration | = 70% |
| | Initial Acid Concentration | = 15.5 M |
| | Final Acid Concentration | = 9.5 M |
| Membrane: | Perfluorosulfonic Acid Polymer | |
| | Thickness | 5 mil. |
| | Equivalent Weight | 1200 |

| Nitrotoluene on Toluene Side (% wt./vol.) | Benzaldehyde on Toluene Side (% wt./vol.) | Reaction Time (minutes) |
|---|---|---|
| 0 | 0 | 0 |
| 0 | 0 | 10 |
| 0 | 0 | 25 |
| 1.2 | 0 | 50 |
| 1.8 | 0 | 60 |
| 2.9 | .09 | 90 |
| 4.2 | .13 | 120 |
| 5.3 | .20 | 150 |
| 6.2 | .27 | 180 |
| 7.8 | .33 | 240 |
| 12.1 | .89 | 360 |

TABLE IX-continued
STATIC NITRATION OF TOLUENE

| 26.0 | .85 | 1560 |
| 25.0 | .91 | 1620 |

TABLE X
STATIC NITRATION OF ANISOLE

| Conditions: | Temperature | = 70°C. |
| | Nitric Acid Concentration | = 70% |
| | Initial Acid Concentration | = 15.5 M |
| | Final Acid Concentration | = About 8 M |
| Membrane: | Perfluorosulfonic Acid Polymer | |
| | Thickness | 5 mil. |
| | Equivalent Weight | 1200 |

| Nitroanisole on Anisole Side (% wt./vol.) | Reaction Time (minutes) |
|---|---|
| 1.5 | 15 |
| 3.5 | 30 |
| 9.5 | 60 |
| 14.5 | 100 |
| 16.5 | 120 |
| 19.7 | 150 |
| 21.8 | 180 |
| 24.7 | 240 |
| 23.2 | 300 |
| 28.0 | 360 |
| 26.7 | 420 |
| 28.3 | 1440 |
| 27.7 | 1560 |
| 28.0 | 1680 |
| 27.3 | 1800 |

What is claimed is:

1. In a process for the nitration of organic compounds which comprises contacting the organic compound with a nitrating agent at a temperature and pressure sufficient to form a nitrated reaction product, the improvement which comprises maintaining the nitrating agent and the organic compound substantially separated by means of a membrane, said membrane being substantially chemically inert to the action of both the organic compound and the nitration agent.

2. The process of claim 1 wherein said membrane is a perfluorosulfonic acid polymer.

3. The process of claim 2 wherein the organic compound is an aromatic compound.

4. The process of claim 2 wherein said aromatic compound is selected from the group consisting of benzene, toluene, xylene and anisole.

5. The process of claim 2 wherein said nitration agent comprises nitric acid.

6. The process of claim 2 wherein said nitration agent comprises from 5 to 100 weight percent nitric acid in an aqueous medium.

7. The process of claim 6 wherein said nitrating agent additionally comprises sulfuric acid.

8. The process of claim 2 wherein said perfluorosulfonic acid membrane is in the form of a hollow fiber.

9. The process of claim 2 wherein said perfluorosulfonic acid membrane has an equivalent weight of 900 to 1700.

10. The process of claim 2 wherein said aromatic compound is benzene.

* * * * *